United States Patent
Yang et al.

(10) Patent No.: US 8,277,786 B2
(45) Date of Patent: Oct. 2, 2012

(54) ODOR CONTROLLED PERSONAL CARE COMPOSITIONS CONTAINING HYDROXYPROPYL TRIALKYLAMMONIUM SALTS

(75) Inventors: Lin Yang, Woodbridge, CT (US); Neil Patrick Randle, Sandy Hook, CT (US); Stephen Roy Barrow, Trumbull, CT (US); Miguel Ortiz, Westport, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 746 days.

(21) Appl. No.: 12/348,354

(22) Filed: Jan. 5, 2009

(65) Prior Publication Data

US 2010/0173998 A1 Jul. 8, 2010

(51) Int. Cl.
*A61K 8/18* (2006.01)
*A61K 8/00* (2006.01)

(52) U.S. Cl. .......... 424/69; 424/65; 424/68; 424/73; 510/119; 510/130; 510/212; 510/432; 510/504

(58) Field of Classification Search .......... None
See application file for complete search history.

(56) References Cited

U.S. PATENT DOCUMENTS

| | | | |
|---|---|---|---|
| 5,648,083 A * | 7/1997 | Blieszner et al. | 424/402 |
| 7,087,560 B2 | 8/2006 | Mc Manus et al. | |
| 7,176,172 B2 | 2/2007 | Harding et al. | |
| 7,282,471 B2 | 10/2007 | Harichian et al. | |
| 2006/0089277 A1 | 4/2006 | Harding et al. | |
| 2006/0263399 A1 * | 11/2006 | Yasuno et al. | 424/401 |
| 2007/0299284 A1 | 12/2007 | Deavenport et al. | |

FOREIGN PATENT DOCUMENTS

| | | |
|---|---|---|
| EP | 1 807 041 B1 | 1/2008 |
| EP | 1 804 922 B1 | 2/2008 |
| WO | 2006/045584 A1 | 5/2006 |
| WO | 2007/094806 A1 | 8/2007 |

OTHER PUBLICATIONS

International Search Report PCT/EP2009/067923.

* cited by examiner

*Primary Examiner* — Lezah Roberts
*Assistant Examiner* — Nannette Holloman
(74) *Attorney, Agent, or Firm* — Edward A. Squillante, Jr.

(57) ABSTRACT

A personal care composition is provided which includes from 0.1 to 30% of a dihydroxypropyltri($C_1$-$C_3$ alkyl) ammonium salt by weight of the composition; from 0.0001 to 0.005% of a tri($C_1$-$C_3$ alkyl)amine or protonated form thereof by weight of the ammonium salt; from 0.002 to 15% of an aluminum salt by weight of the composition; and a cosmetically acceptable carrier wherein the composition has a pH ranging from 5.5 to 6.9. Unpleasant amine odor from trialkyl amines which arise from the dihydroxypropyltri($C_1$-$C_3$ alkyl) ammonium salts is suppressed by the aluminum salt and by careful control of pH conditions.

9 Claims, No Drawings

ODOR CONTROLLED PERSONAL CARE COMPOSITIONS CONTAINING HYDROXYPROPYL TRIALKYLAMMONIUM SALTS

BACKGROUND OF THE INVENTION

1. Field of the Invention

The invention concerns control of odor arising from the presence of hydroxypropyl trialkylammonium salts in personal care compositions.

2. The Related Art

Hydroxypropyl trialkylammonium salts have a number of beneficial cosmetic properties. Foremost is the ability of these salts to moisturize skin. The moisturization benefits have been revealed in U.S. Pat. No. 7,087,560 B2 (McManus et al.), EP 1 807 041 B1 (Unilever), EP 1 804 922 B1 (Unilever) and U.S. Pat. No. 7,282,471 B2 (Harichian et al.).

Another benefit of these salts is that they can mediate the signs of aging. This benefit is reported in U.S. Pat. No. 7,176,172 B2 (Harding et al.).

In developing dihydroxypropyl trialkylammonium salt containing personal care compositions, there has been noted a malodor problem. Off-odors have been attributed to small amounts of low molecular weight trialkylamine continuously being generated from the salt compositions. Even small amounts of amine are readily detected by the human nose.

U.S. Patent Application Publication 2007/0299284 A1 (Deavenport et al.) discloses attempts to inhibit malodors from dihydroxypropyl trialkylammonium salts. Their solution is to reduce the pH of the intermediate reaction leading to the final quaternary ammonium salts. No guidance is provided on controlling odor of personal care compositions that may contain the salts.

Accordingly, the present invention is focused upon reducing malodour arising from volatile trialkylamine which is generated by dihydroxypropyl trialkylammonium salts in a formulated personal care composition.

SUMMARY OF THE INVENTION

A personal care composition is provided which includes:
(i) from 0.1 to 30% of a dihydroxypropyltri($C_1$-$C_3$ alkyl) ammonium salt by weight of the composition;
(ii) from 0.0001 to 0.005% of a tri($C_1$-$C_3$ alkyl)amine or protonated form thereof by weight of the dihydroxypropyltri ($C_1$-$C_3$ alkyl) ammonium salt;
(iii) from 0.002 to 15% of an aluminum salt by weight of the composition; and
(iv) a cosmetically acceptable carrier, wherein the composition has a pH ranging from 5.5 to 6.9.

DETAILED DESCRIPTION OF THE INVENTION

Now it has been found that aluminum salts can inhibit malodor formation resultant from decomposition of dihydroxypropyl tri($C_1$-$C_3$ alkyl) ammonium salts. It has further been found that generation of odor causing trialkylamines can be inhibited by formulating at a pH ranging from 5.5 to 6.9, preferably from 6.0 to 6.8, and optimally from 6.2 to 6.8.

Accordingly, a first element of the present invention is the dihydroxypropyl tri($C_1$-$C_3$ alkyl) ammonium salts. Ordinarily the $C_1$-$C_3$ alkyl constituent of the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salts of this invention. The anion may be organic or inorganic with proviso that the material is cosmetically acceptable.

Typical inorganic anions are halides, sulfates, phosphates, nitrates and borates. Most preferred are the halides, especially chloride. Organic anionic counter ions include methosulfate, toluoyl sulfate, acetate, citrate, tartrate, glycolate, lactate, gluconate, and benzenesulfonate.

Dihydroxypropyltri($C_1$-$C_3$ alkyl)ammonium salts may be obtained via a variety of synthetic procedures, most particularly by hydrolysis of chlorohydroxypropyltri($C_1$-$C_3$ alkyl) ammonium salts. A most preferred species is 2,3-dihydroxypropyltrimonium chloride, wherein the $C_1$-$C_3$ alkyl is a methyl group.

Amounts of the dihydroxypropyl tri($C_1$-$C_3$ alkyl) ammonium salts may range from about 0.1 to about 30%, preferably from about 0.5 to about 20%, optimally from about 1% to about 12% by weight of the composition.

Trialkylamine arising from decomposition of the dihydroxypropyl tri($C_1$-$C_3$ alkyl)amine salts must be minimized. However, any steps to totally suppress amine by pH manipulation will adversely effect stability in the salts. For this reason, a small amount of tri($C_1$-$C_3$ alkyl)amine and/or protonated form thereof should be maintained within the compositions. These small amounts are insufficient to be aesthetically smelly but sufficient to provide a balance against decomposition. Thus, the tri($C_1$-$C_3$ alkyl)amine and protonated form thereof in compositions of this invention ordinarily will be present in amounts from 0.0001 to 0.005, preferably from 0.0001 to 0.001, more preferably from 0.0001 to 0.0005, and optimally from 0.0001 to 0.0003% by weight of the dihydroxypropyltri($C_1$-$C_3$ alkyl) ammonium salts but insufficient in concentration to exhibit a detectable odor (based on nose detection by 80% of a human sniff panel). A particular amine present in the compositions of this invention is trimethylamine and its protonated form trimethylamine hydrochloride. The protonated form of tri($C_1$-$C_3$ alkyl)amine is obtained from neutralization with a hydroacid such as hydrochloric.

Aluminum salts are a further component of compositions according to the present invention. A wide variety of aluminum bearing organic and inorganic substances are suitable for the present invention. Advantageously the aluminum salt is one easily dissociable in water. Preferably the aluminum salt has a solutility of at least 0.5 gram, especially at least 3 gram, and optimally at least 20 gram per 100 ml of water at 20° C. Illustrative but not limiting examples of aluminum salts include aluminum chloride, aluminum acetate, aluminum bromide, aluminum nitrate, aluminum stearate, aluminum acetate, aluminum sulfate, aluminum Lakes, aluminum citrate, aluminum lactate and mixtures thereof. Amounts of the aluminum salt may range from about 0.002 to 15%, preferably from about 0.005 to about 1%, more preferably from about 0.01 to about 0.1%, and optimally from about 0.02 to 0.05% by weight of the composition.

By the term personal care composition is meant any substance applied to a human body for improving appearance, cleansing, odor control or general aesthetics. Nonlimiting examples of personal care compositions include leave-on skin liquid products, shower gels, toilet bars, antiperspirants, deodorants, shave creams, depilatories, lipsticks, foundations, mascara, sunless tanners and sunscreen formulas. Personal care compositions of the present invention may be in any form. These forms may include lotions, creams, roll-on formulations, sticks, mousses, aerosol and non-aerosol sprays and fabric (e.g. nonwoven textile)-applied formulations such as via adhesive patches or via wipes.

Compositions of this invention may also include a cosmetically acceptable carrier. Amounts of the carrier may range from about 1 to about 99.9%, preferably from about 70 to about 95%, optimally from about 80 to about 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, natural or synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to $0.1 \text{ m}^2/\text{s}$ at 25° C. Among the preferred nonvolatile emollients useful in the present compositions are the polydimethyl siloxanes having viscosities from about $1 \times 10^{-5}$ to about $4 \times 10^{-4} \text{m}^2/\text{s}$ at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
a) Alkyl esters of saturated fatty acids having 10 to 24 carbon atoms. Examples thereof include behenyl neopentanoate, isononyl isonanonoate, isopropyl myristate and octyl stearate.
b) Ether-esters such as fatty acid esters of ethoxylated saturated fatty alcohols.
c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
d) Wax esters such as beeswax, spermaceti wax and tribehenin wax.
e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Humectants may be employed in the present invention. These are generally polyhydric alcohol-type materials. Typical polyhydric alcohols include glycerin, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 25%, and optimally from 10 to 20% by weight of the composition.

Surfactants may also be present in compositions of the present invention. Total concentration of the surfactant when present may range from about 0.1 to about 90%, preferably from about 1 to about 40%, optimally from about 0.1 to about 20% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Useful amphoteric surfactants include cocoamidopropyl betaine, $C_{12}$-$C_{20}$ trialkyl betaines, sodium lauroamphoacetate, and sodium laurodiamphoacetate.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Sunscreen agents may also be included in compositions of the present invention. Particularly preferred are such materials as ethylhexyl p-methoxycinnamate, available as Parsol MCX®, Avobenzene, available as Parsol 17890 and benzophenone-3, also known as Oxybenzone. Inorganic sunscreen actives may be employed such as microfine (e.g. from 0.1 to 200 micron average size) titanium dioxide and zinc oxide. Amounts of the sunscreen agents when present may generally range from 0.1 to 30%, preferably from 2 to 20%, optimally from 4 to 10% by weight of the composition.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynlbutylcarbamate and benzyl alcohol. The preservatives should be selected having regard for the use of the composition and possible incompatibilities between the preservatives and other ingredients. Preservatives are preferably employed in amounts ranging from 0.0001% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Another type of useful substance can be that of an enzyme such as elastases, amylases, oxidases, proteases, lipases and combinations.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, cinnamonum ilicioides, aloe vera, grape seed, citrus unshui, willowbark, sage, thyme and rosemary.

Also included may be such materials as lipoic acid, retinoxytrimethylsilane (available from Clariant Corp. under the Silcare 1M-75 trademark), dehydroepiandrosterone (DHEA), flavanoids and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

A wide variety of packaging can be employed to store and deliver the personal care compositions. Packaging is often dependent upon the type of personal care end-use. For instance, leave-on skin lotions and creams and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film. All of the aforementioned are considered packaging within the context of the present invention.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

A lotion illustrative of the present invention is outlined in Table I below. This formula incorporates a 2,3-dihydroxypropyl trimethylammonium chloride salt and a citric acid/sodium citrate buffer to achieve a pH of 5.5. A small amount of trimethylamine is present.

TABLE I

| INGREDIENT* | WEIGHT % |
|---|---|
| PHASE A | |
| Water | Balance |
| Disodium EDTA | 0.05 |
| Methyl Paraben | 0.15 |
| Aluminum Chloride | 0.60 |
| Triethanolamine | 1.20 |
| 2,3-Dihydroxypropyl trimethylammonium Chloride | 1.00 |
| Citric Acid/Sodium Citrate | ** |
| PHASE B | |
| Xanthan Gum | 0.20 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| PHASE D | |
| Vitamin A Palmitate | 0.10 |
| Bisabolol | 0.01 |
| Vitamin A Acetate | 0.01 |
| Fragrance | 0.03 |
| Retinol 50C | 0.02 |
| Conjugated Linoleic Acid | 0.50 |

*0.00005% trimethylamine present.
**Amount sufficient to achieve pH 5.5.

EXAMPLE 2

A shampoo composition useful in the context of the present invention is described in Table II below.

TABLE II

| Ingredient* | Weight % |
|---|---|
| Ammonium Laureth Sulfate | 12.00 |
| Ammonium Lauryl Sulfate | 2.00 |
| Cocoamidopropyl Betaine | 2.00 |
| Sodium Lauroamphoacetate | 2.00 |
| Glycerin | 12.00 |
| 2,3-Dihydroxypropyl Ethyldimethylammonium Sulfate | 5.50 |
| Ethylene Glycol Distearate | 1.50 |
| Cocomonoethanolamide | 0.80 |
| Cetyl Alcohol | 0.60 |
| Polyquaternium-10 | 0.50 |
| Dimethicone | 1.00 |
| Zinc Pyridinethione | 1.00 |
| Citric Acid | 0.39 |
| Sodium Xylene Sulfonate | 1.00 |
| Fragrance | 0.40 |
| Aluminum Acetate | 0.25 |
| Kathon CG ® | 0.0008 |
| Benzyl Alcohol | 0.0225 |
| Citric Acid/Sodium Citrate | ** |
| Water | Balance |

*0.00001% ethyl dimethylamine present
**Amount of citric acid/sodium citrate sufficient to achieve pH 6.2.

EXAMPLE 3

Experiments were conducted to evaluate the effect of various metal ions to improve stability of 2,3-dihydroxypropyl trimethylammonium chloride (hereinafter "DPAC") in controlling decomposition into trimethylammonium hydrochloride (hereinafter TMA.HCl). Samples for these experiments utilized DPAC at 50% in an aqueous system with different specified metal ion sources. The samples were prepared by either of the following two methods: (1) Non-buffered condition: a mixture of DPAC and metal ion salt were titrated by either hydrochloric acid or sodium hydroxide to achieve a pH around 6.2; or (2) Buffered condition: wherein DPAC and the metal ion salt were mixed with 0.1 M phosphate buffer of pH 6.2. Mixtures of the DPAC and metal ion salt were stored at different temperature conditions and the TMA.HCl level was monitored at specified storage time intervals.

In the first set of experiments, aluminum chloride was evaluated under a buffered pH of 6.2. The aluminum ion at 0.025% (250 ppm) level was found to suppress the formation of TMA.HCl, especially at storage temperatures higher than ambient. See Table III.

TABLE III

| | Storage Temperature, ° C.* | | |
|---|---|---|---|
| | Ambient | 40° C. | 50° C. |
| 2 week | | | |
| Control (DPAC) | 1.61 | 2.8 | 3.73 |
| Aluminum Chloride and DPAC | 1.9 | 1.8 | 1.7 |
| 4 week | | | |
| Control (DPAC) | 2 | 4.84 | 7.01 |
| Aluminum Chloride and DPAC | 2.63 | 2.55 | 3.03 |
| 12 week | | | |
| Control (DPAC) | 4.62 | — | 13.19 |
| Aluminum Chloride and DPAC | 3.19 | — | 5.14 |

*Numbers reported in this Table are for TMA.HCl multiplied by $10^{-4}$ weight % with experimental error of +/−0.3 × $10^{-4}$ weight %.

Experiments were also conducted to determine the effect of aluminum potassium sulfate under a buffered pH of 6.2. Level of aluminum ion was 0.025% (250 ppm). Once again, it is evident from Table IV that aluminum ions can slow the TMA.HCl formation, especially at storage temperatures higher than ambient.

TABLE IV

| | Storage Temperature, ° C.* | |
|---|---|---|
| | Ambient | 50° C. |
| 2 week | | |
| Control (DPAC) | 4.42 | 11.45 |
| Aluminum Potassium Sulfate and DPAC | 3.77 | 3.58 |

TABLE IV-continued

|  | Storage Temperature, °C.* | |
|---|---|---|
|  | Ambient | 50° C. |
| 4 week | | |
| Control (DPAC) | 5.06 | 14.34 |
| Aluminum Potassium Sulfate and DPAC | 3.88 | 3.64 |

*Numbers reported in this Table are for TMA.HCl multiplied by $10^{-4}$ weight % with experimental error of +/−0.3 × $10^{-4}$ weight %.

Effect of aluminum silicate was also evaluated at 0.025% (250 ppm) level of aluminum ion. The employed media was un-buffered with the pH being set at approximately 6.2. Again it is seen that aluminum ion, this time from aluminum silicate slows down the TMA.HCl formation from a DPAC containing medium.

TABLE V

|  | Storage Temperature, °C.* | |
|---|---|---|
| 2 week | Ambient | 50° C. |
| Control (DPAC) | 3.22 | 5.18 |
| Aluminum Silicate and DPAC | 3.56 | 3.93 |

*Numbers reported in this Table are for TMA.HCl multiplied by $10^{-4}$ weight % with experimental error of +/−0.3 × $10^{-4}$ weight %.

Still further experiments were conducted to determine the effect of other metal ions. Magnesium ion was evaluated at 0.005% (50 ppm) generated from magnesium sulfate. Calcium ion was evaluated at a level of 0.025% (250 ppm) generated from calcium chloride. Evaluations were performed in an un-buffered system where pH was 6.2 throughout storage. Results are recorded in Table VI as to their effect upon formation of TMA.HCl. It was found that within experimental error (+/−0.3×$10^{-4}$ weight %), the level of TMA.HCl was not be effected by the presence of calcium or magnesium ions.

TABLE VI

|  | Storage Temperature, °C.* | | |
|---|---|---|---|
|  | Ambient | 40° C. | 50° C. |
| 2 week | | | |
| Control (DPAC) | 3.05 | 3.28 | 3.69 |
| Calcium Chloride and DPAC | 2.52 | 3.19 | 3.26 |
| Magnesium Sulfate and DPAC | 2.95 | 3.19 | 3.80 |
| 4 week | | | |
| Control (DPAC) | 2.82 | 3.74 | 4.88 |
| Calcium Chloride and DPAC | 2.79 | 3.88 | 4.64 |
| Magnesium Sulfate and DPAC | 2.76 | 3.83 | 4.29 |
| 8 week | | | |
| Control (DPAC) | 3.17 | — | 5.93 |
| Calcium Chloride and DPAC | 2.77 | — | 5.38 |
| Magnesium Sulfate and DPAC | 3.20 | — | 5.53 |

*Numbers reported in this Table are for TMA.HCl multiplied by $10^{-4}$ weight % with experimental error of +/−0.3 × $10^{-4}$ weight %.

Levels of ferric ion at 0.005 weight % (50 ppm) were evaluated for their effect on TMA.HCl formation during DPAC storage. The system was buffered to 6.2. Results are found in Table VII. In these experiments it is seen that ferric ion had a negative effect in controlling TMA.HCl formation.

TABLE VII

|  | Storage Temperature, °C.* | | |
|---|---|---|---|
|  | Ambient | 40° C. | 50° C. |
| 2 week | | | |
| Control (DPAC) | 1.61 | 2.80 | 3.73 |
| Ferric Chloride and DPAC | 4.52 | 5.38 | 4.94 |
| 4 week | | | |
| Control (DPAC) | 2.00 | 4.84 | 7.01 |
| Ferric Chloride and DPAC | 5.52 | 7.37 | 9.61 |
| 8 week | | | |
| Control (DPAC) | 4.62 | — | 13.19 |
| Ferric Chloride and DPAC | 6.60 | — | 19.47 |

*Numbers reported in this Table are for TMA.HCl multiplied by $10^{-4}$ weight % with experimental error of +/−0.3 × $10^{-4}$ weight %.

A set of experiments were also done to evaluate the effect of aluminum chloride 0.0250 weight % (250 ppm) on formation of TMA.HCl at an unbuffered pH of 3.8. Table VIII below reports observations. At low pH such as 3.8, the rate of formation of TMA.HCl is greater than in the absence thereof.

TABLE VIII

|  | Storage Temperature, °C.* | | |
|---|---|---|---|
| 2 week | Ambient | 40° C. | 50° C. |
| Control (DPAC) | 3.99 | 4.16 | 4.67 |
| Aluminum Chloride and DPAC | 4.60 | 5.64 | 6.78 |

*Numbers reported in this Table are for TMA.HCl multiplied by $10^{-4}$ weight % with experimental error of +/−0.3 × $10^{-4}$ weight %.

What is claimed is:

1. A personal care composition comprising:
   (i) from 0.1 to 30% of a dihydroxypropyltri($C_1$-$C_3$ alkyl) ammonium salt by weight of the composition;
   (ii) from 0.0001 to 0.005% of a tri($C_1$-$C_3$ alkyl) amine or protonated form thereof by weight of the dihydroxypropyltri ($C_1$-$C_3$ alkyl) ammonium salt;
   (iii) from 0.002 to 0.1% of an aluminum salt by weight of the composition; and
   (iv) a cosmetically acceptable carrier, wherein the composition has a pH ranging from 5.5 to 6.9.

2. The composition according to claim 1 wherein the ammonium salt is dihydroxypropyl trimethylammonium salt.

3. The composition according to claim 1 wherein the tri ($C_1$-$C_3$ alkyl) amine or protonated form thereof is present in an amount from 0.0001 to 0.001% by weight of the dihydroxypropyltri ($C_1$-$C_3$ alkyl) ammonium salt.

4. The composition according to claim 1 wherein the aluminum salt is selected from the group consisting of aluminum chloride, aluminum acetate, aluminum bromide, aluminum nitrate, aluminum stearate, aluminum sulfate, aluminum Lakes, aluminum citrate, aluminum lactate and mixtures thereof.

5. The composition according to claim 1 wherein the aluminum salt is present in an amount from 0.02 to 0.05% by weight of the composition.

6. The composition according to claim 1 wherein the amine is trimethylamine.

7. The composition according to claim 1 wherein the pH ranges from 6.0 to 6.8.

8. The composition according to claim 1 further comprising a surfactant present in an amount from 0.1 to 20% by weight of the composition.

9. The composition according to claim 1 further comprising glycerin in an amount from 10 to 20% by weight of the composition.

* * * * *